(12) United States Patent
Vermeiden

(10) Patent No.: US 11,083,700 B2
(45) Date of Patent: Aug. 10, 2021

(54) BUTYRATE SALTS FOR USE IN INFLAMMATORY DISEASES

(71) Applicant: BirrBeheer B.V., Vreeland (NL)

(72) Inventor: Jan Pieter Willem Vermeiden, Vreeland (NL)

(73) Assignee: BIRRBEHEER B.V., AG Vreeland (NL)

( * ) Notice: Subject to any disclaimer, the term of this patent is extended or adjusted under 35 U.S.C. 154(b) by 0 days.

(21) Appl. No.: 16/600,660

(22) Filed: Oct. 14, 2019

(65) Prior Publication Data

US 2020/0038351 A1 Feb. 6, 2020

Related U.S. Application Data

(63) Continuation of application No. 15/779,177, filed as application No. PCT/NL2016/050830 on Nov. 25, 2016, now abandoned.

(30) Foreign Application Priority Data

Nov. 27, 2015 (NL) .................................... 2015874

(51) Int. Cl.
| | | |
|---|---|---|
| *A61K 31/19* | (2006.01) | |
| *A61P 25/06* | (2006.01) | |
| *A61P 25/16* | (2006.01) | |
| *A61P 5/00* | (2006.01) | |
| *A61P 25/14* | (2006.01) | |
| *A61K 9/50* | (2006.01) | |
| *A61K 9/48* | (2006.01) | |
| *A61K 31/194* | (2006.01) | |

(52) U.S. Cl.
CPC ............ *A61K 31/19* (2013.01); *A61K 9/4875* (2013.01); *A61K 9/5015* (2013.01); *A61K 31/194* (2013.01); *A61P 5/00* (2018.01); *A61P 25/06* (2018.01); *A61P 25/14* (2018.01); *A61P 25/16* (2018.01); *A61K 9/4808* (2013.01)

(58) Field of Classification Search
CPC .... A61K 31/19; A61K 31/194; A61K 9/5015; A61K 9/4875; A61K 9/4808; A61P 25/14; A61P 5/00; A61P 25/16; A61P 25/06

See application file for complete search history.

(56) References Cited

U.S. PATENT DOCUMENTS

| | | | |
|---|---|---|---|
| 2005/0272647 A1* | 12/2005 | Yamaji ............... | A61K 31/4045 514/16.6 |
| 2007/0004639 A1 | 1/2007 | Kane et al. | |
| 2011/0077300 A1 | 3/2011 | Ye et al. | |
| 2013/0115280 A1 | 5/2013 | Moro | |

FOREIGN PATENT DOCUMENTS

| | | | | | |
|---|---|---|---|---|---|
| FR | 2 762 212 | A1 | 10/1998 | | |
| GB | 2 466 041 | A | 6/2010 | | |
| GB | 2466041 | A | * 6/2010 | ........... | A23K 20/105 |
| WO | 01/78704 | A2 | 10/2001 | | |
| WO | 2005/112931 | A2 | 12/2005 | | |
| WO | 2008/091170 | A1 | 7/2008 | | |

OTHER PUBLICATIONS

Paolo Sossai, Butyric acid: what is the future for this old substance?, Swiss Med Wkly. 2012;142:w13596 (Year: 2012).*
Netherlands Search Report and Written Opinion of Application No. 2015874 dated Jul. 21, 2016.
International Search Report and Written Opinion of Application No. PCT/NL2016/050830 dated Feb. 14, 2017.
Baso Giuseppina Mattice et al., "Effects of Sodium Butyrate and Its Synthetic Amide Derivative on Liver Inflammation and Glucose Tolerance in an Animal Model of Steatosis Induced by High Fat Diet", PLOS One, deel 8, nr. 7, Jul. 2013 (Jul. 2013).
Ankesh Kukkar et al., "Attenuation of neuropathic pain by sodium butyrate in an experimental model of chronic constriction injury in rats", Jounral of the Formosan Medical Association, deel 113, nr. 12, Dec. 1, 2014 (Dec. 1, 2014).
"Normal intestinal microbiota in the aetiopathogenesis of rheumatoid arthritis", Professor P Toivanen, Department of Medical Microbiology, Turku, University, Kiinamyllynkatu, 3, FIN-20520 Turku, Finland, Accepted May 12, 2003, www.annrheumdis.com, pp. 807-811.
"Plasma Concentration of Interleukin-6 and the Risk of Future Myocardial Infarction Among Apparently Healthy Men", Jaul M. Ridker, MD et al., Downloaded from http://circ.ahajournals.org/ by guest on Oct. 12, 2015, Circulation Apr. 18, 2000, pp. 1767-1772.
"Butyric acid in functional constipation", Aleksandra Pituch et al., Prz Gastroenterol 2013; 8 (5): 295-298 DOI: 10.5114/pg.2013. 38731, Przeglad Gastroenterologiczny 2013; 8 (5), Received: Sep. 10, 2013, Accepted: Sep. 29, 2013, pp. 295-298.
"Circulating TNF Receptors 1 and 2 Predict ESRD in Type 2 Diabetes", Monika A. Niewczas et al., J Am Soc Nephrol 23: 507-515, 2012. doi: 10.1681/ASN.2011060627, ISSN : 1046-6673/ 2303-507, www.jasn.org, Received Jun. 28, 2011, Accepted Nov. 1, 2011, pp. 507-515.

(Continued)

*Primary Examiner* — Sarah Pihonak
*Assistant Examiner* — Jason Deck
(74) *Attorney, Agent, or Firm* — Thomas|Horstemeyer, LLP

(57) ABSTRACT

This invention relates to preparations comprising a butyrate salt for enteral administration for use in the treatment of conditions and diseases that are not diseases or conditions of the intestine and/or are associated with systemic inflammation. Preparations comprising a butyrate salt for enteral administration were found useful in the treatment of osteoarthritis, Parkinson's disease, migraine, idiopathic subfertility, hangovers, and gout.

19 Claims, No Drawings

(56) References Cited

OTHER PUBLICATIONS

"Microencapsulated sodium butyrate administered to patients with diverticulosis decreases incidence of diverticulitis—a prospective randomized study", Lukasz Krokowicz et al., Accepted: Nov. 20, 2013 /Published online: Dec. 18, 2013, The Author(s) 2013. This article is published with open access at Springerlink.com, Int J Colorectal Dis (2014) 29:387-393, DOI 10.1007/s00384-013-1807-5, pp. 387-393.

"Sodium butyrate and short chain fatty acids in prevention of travellers' diarrhoea: A randomized prospective study", Lukasz Krokowicz et al., Received Apr. 22, 2013; received in revised form Jul. 19, 2013; accepted Aug. 28, 2013, Please cite this article in press as: Krokowicz L, et al., Sodium butyrate and short chain fatty acids in prevention of travellers' diarrhoea: A randomized prospective study, Travel Medicine and Infectious Disease (2013), http://dx.doi.org/10.1016/j.tmaid.2013.08.008, pp. 1-6.

"Butyrate sensitizes human colon cancer cells to TRAIL-mediated apoptosis", Ambrosio Hernandez, MD et al., From the Department of Surgery, The University of Texas Medical Branch, Galveston, Tex, Supported by grants R01 AG10885, R01 DK48498, P01 DK35608, and T32 DK07639 from the National Institutes of Health, Presented at the 62nd Annual Meeting of the Society of University Surgeons, Chicago, III, Feb. 8-10, 2001, Reprint requests: B. Mark Evers, MD, Department of Surgery, The University of Texas Medical Branch, 301 University Blvd, Galveston, TX 77555-0536.

Miller AA, Kurschel E, Osieka R, Schmidt CG, "Clinical pharmacology of sodium butyrate in patients with acute leukemia", Eur J Cancer Clin Oncol. Sep. 1987;23(9):1283-T PMID: 3678322. [Attachment A].

Korsten et al., "Modeling of the luminal butyrate concentration to design an oral formulation capable of achieving a pharmaceutical response", PharmaNutrition 10 (2019) 100166; 1-6. [Attachment B].

Bloemen et al., "Short chain fatty acids exchange across the gut and liver in humans measured at surgery", Clin Nutr. Dec. 2009;28(6):657-61. [Attachment C].

Robinson et al., "Regulation of the Intestinal Barrier Function by Host Defense Peptides", Front Vet Sci. 2015;(2)57: 1-17 [Attachment D].

Gantois et al., "Butyrate specifically down-regulates salmonella pathogenicity island 1 gene expression", Appl Environ Microbial. 2006;72(1):946-949. [Attachment E].

Ahsan et al., "Sodium butyrate in chicken nutrition: the dynamics of performance, gut microbiota, gut morphology, and immunity" World's Poultry Science Journal, vol. 72, Jun. 2016, pp. 265-275. [Attachment F].

Arpaia et al., "Metabolites produced by commensal bacteria promote peripheral regulatory T cell generation", Nature. Dec. 19, 2013; 504(7480): doi:10.1038/nature12726. [Attachment G].

Z.Y. Huang et al., "Both systemic and local lipopolysaccharide (LPS) burden are Q6 associated with knee OA severity and inflammation", and Osteoarthritis and Cartilage YJOCA3760_proof, May 27, 2016, 1/7. [Attachment H].

Zeyu Huang et al., "Does lipopolysaccharide-mediated inflammation have a role in OA?", Article in Nature Reviews Rheumatology • Dec. 2015, 1-7 •DOI: 10.1038/nrrheum. 2015.158. [Attachment I].

Tahli Singer-Englar et al., "Obesity, diabetes, and the gut microbiame: an updated review", Expert Review of Gastroenterology & Hepatology, 2019, (13)1:3-15. [Attachment J].

* cited by examiner

BUTYRATE SALTS FOR USE IN INFLAMMATORY DISEASES

CROSS-REFERENCE TO RELATED APPLICATIONS

This application is a Continuation of U.S. patent application Ser. No. 15/779,177, filed May 25, 2018, which is the National Stage of International Application No. PCT/NL2016/050830, filed Nov. 25, 2016, which claims the benefit of and priority to Netherlands Application No. 2015874, filed on Nov. 27, 2015, the contents of all of which are incorporated by reference as if fully set forth herein.

FIELD OF THE INVENTION

The invention relates to the use of butyrate salts for the treatment of a disease. In particular to the use of such butyrate salts for enteral administration in a gastro-resistant formulation for delivery to the intestine.

BACKGROUND ART

Butyric acid is formed by the microflora of the gut through the digestion of dietary fibres. Butyric acid is also generated as a metabolite by breakdown of fats, carbohydrates and proteins, and it is further metabolized via the fatty acid and tricarboxylic pathways. Sodium butyrate is the sodium salt of butyric acid and is characterized by a solid state that can easily be dissolved in water.

Butyric acid and salts therefrom have been suggested to have beneficial effects in the treatments of diseases of the intestine. Through oral intake, e.g. of encapsulated sodium butyrate, butyrate is delivered to the intestine where it is to have its action. Diseases of the intestine that are to benefit from butyrate include diseases like Crohn's disease, diverticulitis, ulcerative colitis, and diarrhoea (see e.g. Krokowicz et al., Int. Journal of Colorectal Disease, 2014).

Debutir contains encapsulated sodium butyrate (manufactured by Sensilab in Poland) is intended for human use. Globamax formulas (manufactured by Sanluc in Belgium) are dietary food supplements for animal feed containing encapsulated calcium salt of butyric acid. Globamax formulas are for use in animals as growth promotors, immune reinforcement and intestinal health. In addition, butyric acid and salts therefrom are also tested in inhibiting oncogenesis in the colon. It has been shown that butyrate sensitizes human colon cancer cells to apoptosis (Hernandez et al., Surgery, 2001).

Sodium butyrate thereof have been used solely in the treatment of diseases of the intestine such as inflammatory bowel diseases (e.g. Crohn's disease, intestinal inflammation, ulcerative colitis, diverticulitis). Its use for the treatment of diarrhoea has been proven (Krokowicz et al. Travel Med Infect Dis. 2014 March-April; 12(2):183-8) and its use for constipation has been suggested (Pituch et al Prz Gastroenterol. 2013; 8(5):295-8.)

SUMMARY OF THE INVENTION

Surprisingly, the inventors have found that preparations comprising a butyrate salt for enteral administration are not only useful for the treatment of conditions and diseases of the intestine, but are also very useful for the treatment of conditions and diseases that are not diseases or conditions of the intestine. The inventors have found that preparations comprising a butyrate salt for enteral administration are also very useful for the treatment of conditions and diseases that are diseases that are associated with systemic inflammation. Preparations comprising a butyrate salt for enteral administration have now surprisingly been found useful in the treatment of osteoarthritis, arteriosclerosis, rheumatism, psoriasis, multiple sclerosis, Alzheimer's disease, Parkinson's disease, migraine, autism, depression, impaired kidney functioning, idiopathic subfertility, recurrent abortion, recurrent implantation failure, hangovers, and gout. Said diseases are diseases that are not diseases of the intestine but are diseases that are manifested outside of the intestine, i.e. are manifested extra-intestinally. Such diseases that are not diseases of the intestine are diseases of the brain, cardiovascular system, joints, nervous system, skin, kidney and of the female reproductive system.

Without being bound by theory it is believed that such preparations when delivering the active substance butyrate to the intestine, where the butyrate is to have its action, that subjects having conditions and diseases such as listed above that are not related to the intestine will benefit by amelioration or even abrogation of said conditions and diseases or symptoms thereof. Hence, it is understood that it is not an objective of the invention to administer to a subject the preparation comprising a butyrate salt for enteral administration in order to obtain significantly increased systemic levels of butyrate in the subject, e.g. in the bloodstream, high enough such that the effect of the treatment is due to direct action of the butyrate at the site of interest, e.g. the skin, the joints or the brain. Furthermore, any excess butyrate that would not be metabolized by the intestine will end up in the blood and will be delivered to the liver via the hepatic portal vein where it is processed. Hence, any increase in systemic levels of butyrate that is achieved by administering the preparation according to the invention to a subject is considered much too low and negligible that any effect can be attributed thereto.

Rather, without being bound by theory, the effect of butyrate when delivered to the intestine according to the invention includes binding to and/or entering the epithelial cells where it diminishes the paracellular permeability of the intestinal epithelium. Hence, because the permeability of the intestine is reduced, the systemic concentration of bacterial products like lipopolysaccharides and peptidoglycans will be reduced. Such bacterial products can induce the synthesis and release of pro-inflammatory cytokines. Also, butyrate has an anti-inflammatory effect by inhibiting the differentiation to Th1 and ThT17 cells and promoting the formation of regulatory T cells, by reducing the synthesis and release pro-inflammatory cytokines and promoting production of e.g. IL-10, an anti-inflammatory cytokine. Butyrate can bind to the GPR109a, GPR41 and GRR 43 receptors that may trigger an anti-inflammatory cascade. Combined, the inventors now realized that the effect of butyrate when delivered to the intestine can strongly reduce the systemic inflammatory state. The inventors now further realized that because the systemic inflammatory state is reduced, many diseases or conditions that are associated with systemic inflammation may benefit therefrom. In addition, the intestinal epithelium also has Breast Cancer Receptor Protein receptors (BCRP). These receptors are butyrate dependant and are among other things uric acid transporters. Hence, clearance from the blood of uric acid may be increased by the use of butyrate delivered to the intestine. Subjects suffering from inadequate kidney functioning may benefit therefrom, in addition to the reduction of systemic inflammation and, furthermore, subjects suffering from gout can, by the daily use of butyrate delivered to the intestine, live with severely reduced symptoms or even without any symptoms. Hence, the inventors thus found that the effect of butyrate salts when delivered to the intestine is not restricted solely to conditions of the intestine, but found such treatments to be beneficiary for conditions or diseases that are not conditions or diseases of the intestine. Such diseases include diseases that can be associated e.g. with systemic inflammation and/or increased blood levels of uric acid. Hence, in contrast to any of the applications in the prior art, the current invention involves the application of preparations comprising a butyrate salt for enteral administration for the treatment of conditions or diseases that are associated with systemic inflammation and/or that are not diseases of the intestine. No such treatments were considered in the prior art until the current invention was made.

DETAILED DESCRIPTION OF THE INVENTION

In a first aspect, the invention relates to a preparation comprising a butyrate salt for enteral administration wherein the preparation is for use in the treatment of a subject suffering from a disease associated with systemic inflammation. In another aspect, the invention relates to a preparation comprising a butyrate salt for enteral administration wherein the preparation is for use in the treatment of a subject suffering from a disease wherein the disease is not a disease of the intestine. In another aspect the invention relates to a preparation comprising a butyrate salt for enteral administration wherein the preparation is for use in the treatment of a subject suffering from a disease associated with systemic inflammation and wherein the disease is not a disease of the intestine. Preferably, according to the invention, the treatment of subjects involves the treatment of human subjects.

As already explained above, the uses of such preparations per se in the art that are known all relate to the treatment of diseases or conditions of the intestine. In a further aspect, the invention relates to a preparation comprising a butyrate salt for enteral administration wherein the preparation is for use in the treatment of a subject suffering from a disease or condition, wherein the disease or condition is not a disease or condition of the intestine and where said disease or condition of the intestine is inflammatory bowel disease (e.g. Crohn's disease, intestinal inflammation, ulcerative colitis, diverticulitis) or colon cancer.

Systemic inflammation is the result of release of pro-inflammatory cytokines from immune-related cells and activation of the innate immune system. Systemic inflammation is also associated with chronic inflammation. Subjects that may have a relative increase of pro-inflammatory cytokines in blood plasma and that suffer from diseases and conditions that are not diseases or conditions of the intestine may benefit from the administration of the preparation of the invention comprising a butyrate salt for enteral administration. The state of systemic inflammation can be determined by measuring pro-inflammatory cytokines in blood plasma.

Plasma values of pro-inflammatory cytokines can be elevated in apparently healthy subjects. The assessed values of all the subjects can be divided into quartiles (q1, q2, q3 and q4). The quartiles of a ranked set of data values are provided from three determined values (Q1, Q2 and Q3) that separate a data set into four equal groups (q1, q2, q3 and q4) each group comprising a quarter of the data points, in this instance pro-inflammatory cytokines measured in subjects. The first quarter (q1) can be defined as the range below Q1. Q1 is the middle number between the smallest number and the median of the data set. The median is Q2. The second quarter (q2) can be defined as the range between Q1 and Q2. The third quartile (q3) can be defined as the range between Q2 and Q3. Q3 is the middle value between the median and the highest value of the data set. The fourth quartile (q4) can be defined as the range above Q3. The first quarter (q1) can be regarded to be not in a state of systemic inflammation. The $2^{nd}$, $3^{rd}$ and $4^{th}$ quarter (q2, q3 and q4) i. e. above the first quartile, can be regarded to be in a state of systemic inflammation.

For example, in apparently healthy men, the pro-inflammatory cytokine IL-6 was measured in blood plasma (Ridker et al., Circulation, 2001). The concentration of IL-6 in the first quarter was less than 1.04 pg/ml ($1^{st}$ quart. <1.04 pg/ml; range $2^{nd}$ quart. 1.04-1.46 pg/ml; range $3^{rd}$ quart. 1.47-2.28 pg/ml; $4^{th}$ quart. >2.28 pg/ml). Hence, from the analysis of this population, a subject having a concentration higher than 1.04 pg/ml may be regarded to have systemic inflammation. IL-6 can easily be determined using commercially available kits according to the manufacturer's instructions. For example, the Human IL-6 Quantikine ELISA Kit as available from R&D systems may be used (cat. nr. D6050, R&D Systems Inc., Minneapolis, USA). Hence, systemic inflammation can be defined as a condition in a subject wherein at least IL-6 in blood plasma of this subject is above the first quartile, Q1, relative to a population of apparently healthy subjects.

In addition, the pro-inflammatory cytokine soluble TNF Receptor 1 (sTNFR1) can be determined as a measure of systemic inflammation. For example, the Human sTNFRI Quantikine ELISA Kit available from R&D Systems (cat. nr. DRT100, R&D Systems Inc., Minneapolis, USA). For example, said kit was used in a group of patients to determine the inflammatory state (Niewczas et al., J Am Soc Nephrol, 2012). The sTNFR1 concentration in plasma was determined and subjects in the first quarter (below the first quartile) had a concentration of less than 1049 pg/ml ($1^{st}$ quart. <1049 pg/ml; range $2^{nd}$ quart. 1049-1310 pg/ml; range $3^{rd}$ quart. 1311-1837 pg/ml; $4^{th}$ quart. >1837 pg/ml). Hence, from the analysis of this population, in general a subject having a concentration higher than 1049 pg/ml may be regarded to have systemic inflammation. Systemic inflammation can also be defined as a condition in a subject wherein at least sTNFR1 in blood plasma of this subject is above the first quartile, Q1, relative to a population of apparently healthy subjects.

Hence, it can easily be determined whether a subject can be regarded to have systemic inflammation by determining the plasma concentration of pro-inflammatory cytokines in a subject population and determine whether or not the subject falls within the range above the first quartile or not. Hence, the concentration pro-inflammatory cytokines in the blood plasma, such as sTNFR1 and/or IL-6, is determined and compared with blood plasma concentrations from a population, and when a subject suffering from a disease that may be associated with systemic inflammation has a plasma concentration that is within the second, third of fourth quartile, such a subject may benefit from the treatment with butyrate in accordance with the invention.

In one embodiment, a subject is considered to have systemic inflammation when the subject has a concentration of IL-6 and/or sTNFR1 in blood plasma that falls in the range of the second, third and fourth quartile. Such blood plasma concentrations may be determined using the kits with cat. nrs. D6050 and/or DRT100 as available from R&D Systems Inc., Minneapolis, USA. Such subjects may be considered to have systemic inflammation when such kits are used to determine the concentration of IL-6 and/or sTNFR1 and the concentration for IL-6 is higher than e.g. 1.04 pg/ml and/or for sTNFR1 is higher than e.g. 1049 pg/ml. It is understood that absolute measurement values of IL-6 and sTNFR1 may vary depending on the measurement conditions and/or the assay used.

It may not be a requirement of the invention to determine the inflammatory state of a subject. Subjects suffering from a disease that is associated with systemic inflammation and/or that is not a disease of the intestine, such as disclosed herein, may use the preparations comprising butyrate salt for enteral administration and benefit therefrom without having the inflammatory state determined.

As said, the invention relates to a preparation comprising a butyrate salt for enteral administration wherein the preparation is for use in the treatment of a subject suffering from a disease (or condition) associated with systemic inflammation and/or wherein the disease is not a disease of the intestine. Such preparations in accordance with the invention may be for use in the treatment of a disease or condition selected from the group consisting of osteoarthritis, arteriosclerosis, rheumatism, psoriasis, multiple sclerosis, Alzheimer's disease, Parkinson's disease, migraine, autism, depression, impaired kidney functioning, idiopathic subfertility, recurrent abortion, recurrent implantation failure, hangovers, gout. Without being bound by theory, such diseases or conditions all have in common that these can occur in subjects not suffering from conditions or diseases of the intestine. In accordance with the invention subjects suffering both from conditions or diseases of the intestine and from conditions or diseases that are not of the intestine as disclosed herein may benefit from administering a butyrate salt as well.

It is understood that "a butyrate salt" relates to a pharmaceutically acceptable salt. Such butyrate salts include those compounds of the invention that are safe and effective for use in subjects and that possess the desired biological activity. Suitable base salts include, but are not limited to, calcium, magnesium, potassium, sodium and ammonium The preparation according to the invention comprises a butyrate salt for enteral administration. Enteral administration according to the invention includes administration via the gut, the mouth or stomach. When orally administered, preferably the butyrate salt is comprised in a preparation that is resistant to gastric passage. For example, the butyrate salt may be comprised in a gastric resistant coating.

The preparation comprising a butyrate salt may also be comprised in the form of a repository for insertion in the rectum. Suppositories can be made e.g. by mixing just melted Witepsol H15 (100 grams) with 20 grams Calcium Butyrate (uncoated). The Witepsol H15 melts at temperatures of 33.5-35.5° C. and is a commonly used lipophilic base used for repositories. Under continuously stirring the mixture is poured out in 2.5 ml suppositories moulds. After solidification the moulds were sealed.

Preferably, the preparation comprising a butyrate salt is comprised in a gastro-resistant formulation when orally administered. The gastro-resistant formulation embeds the butyrate salt such that the preparation of butyrate salt can pass through the stomach and gastric tract without substantially releasing the butyrate salt. The term "without substantially releasing the butyrate salt" as used herein means that at least 70%, such as at least 75%, at least 80%, at least 85%, at least 90%, at least 95%, or at least 96%, 97%, 98%, or 99%, or more by weight of the butyrate salt present in the preparation is not released in the stomach and gastric tract, i.e., at most 30%, such as at most 25%, 20%, 15%, 10%, 5%, 4%, 3%, 2%, 1% or less by weight of the butyrate salt present in the preparation is released in the stomach and gastric tract. When the formulation is delivered to the intestine, the butyrate is to become available. Preferably the butyrate salt is made available in the intestinal tract such that butyrate is released along the length of the intestine. Preferably, the gastro-resistant formulation releases the butyrate in an extended way along essentially the entire length of the intestine. Any gastro-resistant formulation may be contemplated that is compatible with the butyrate salt and provides resistance to gastric acid and allows the release, preferably extended release, of the butyrate in the intestine. How to select and design such formulation is described e.g. in the Handbook of Pharmaceutical Controlled Release Technology edited by Donald Wise, 2000. As long as the gastro-resistant formulation results in release of the active ingredient, i.e. butyrate, in the intestine, preferably along the length of the intestine, such a formulation can be contemplated.

Preferably, the use comprises a daily intake of at most 4 grams of butyrate. The formula of the butyrate ion is $C_4H_7O_2^-$ which corresponds to a molar mass of approx. 87.098 g/mol. It is understood that when reference is made to the amount of butyrate used, reference is made to the butyrate ion and does not include the molar mass of the counter ion (e.g. Calcium, Sodium, etc.). For example, when the daily intake of butyrate would consist essentially of the calcium butyrate salt (molar mass approx. 214.234 g/mol), the daily intake of calcium butyrate surmounts to at most about 5 gram (4 gr.×(214.234)/(2*87.078)=4.92 gr.).

Preferably, the butyrate salt that is used is a salt that has a moderate to low solubility in water. By selecting a relatively low solubility in water, the extended intestinal release properties of the preparation can be further improved. When the butyrate salt is released in the intestine from the preparation, the low solubility further results in a gradual release of butyrate when the butyrate salt is passing along the intestine. Having a butyrate salt that is highly soluble, upon release of the butyrate salt from the preparation, the butyrate will be immediately available. Having the butyrate salt as a moderate or low soluble salt will further assist in releasing the butyrate along the length of the intestine. Preferably, the butyrate salt is calcium butyrate. Calcium butyrate can be prepared e.g. by mixing calcium hydroxide (powder) and butyric acid (fluid) in the proper ratio to allow the formation of calcium butyrate:

$$Ca(OH)_2 + 2C_4H_8O_2 \rightarrow Ca(C_4H_7O_2)_2 + 2H_2O$$

Reaction time depends on the size of the reactor, intensity of mixing and cooling control. Preferably, the calcium butyrate provided (or prepared by carrying out the above reaction) according to the invention is dried, ground, water and binding agent are added and sieved to select calcium butyrate granules of a size in the range of 0.5-1.5 mm, preferably 1.0-1.5 mm. It is understood that the butyrate salt may also be a mixture of butyrate salts having different counter ions, e.g. any combination of sodium butyrate, calcium butyrate and further pharmaceutically acceptable butyrate salts. Hence, the butyrate salt does not necessarily consist entirely of a butyrate salt with a single counter ion. Butyrate salts according to the invention are preferably ground and sieved to obtain granules of size in the range of 0.5-1.5 mm, preferably 1.00-1.5 mm. However, any suitable granule size may be selected.

In a further embodiment, the gastro-resistant, and preferably extended intestinal release, formulation that is used to comprise the butyrate salt comprises a natural plant oil.

Preferably, said formulation comprises a natural plant oil comprising triglycerides. Said natural plant oil may be a fraction of a natural plant oil enriched in said triglycerides. For example, such a natural plant oil fraction that may be preferred is hardened palm oil or palm stearin. Palm stearin consists of mostly glyceryl tripalmitate. Hence, the gastro-resistant formulation in accordance with the invention may comprise a triglyceride matrix, wherein preferably said triglyceride matrix may be derived from hardened palm oil. Hence, in one embodiment, the gastro-resistant formulation comprises a triglyceride matrix, and in a further embodiment, said triglyceride matrix comprises hardened palm oil. The butyrate salt granules can be coated with the gastro-resistant formulation. As said, butyrate salts according to the invention are preferably ground and sieved to obtain granules of size in the range of 0.5-1.5 mm, preferably 1.0-1.5 mm. Granules can subsequently be immersed in a bath of liquid hardened palm oil or the like, sieved and tumbled dried. The average thickness of the coating can be about 0.014 mm, or more, depending on the coating process. This way, granules can be obtained that have a core that consists substantially of the butyrate salts and that have a coating that provides for extended intestinal release. The coating prevents the sodium butyrate present in the core of the granule to be released in the stomach or oesophagus. When the granules with the coating arrive in the intestine, lipases degrade the lipid coating and the butyrate salt becomes available for dissolving and butyrate becomes available to have its action.

In one embodiment, said preparation according to the invention, wherein calcium butyrate is comprised in a gastro-resistant formulation, comprises about 50% by weight of calcium butyrate and about 50% by weight of hardened palm oil. Such a formulation comprises about 40% by weight of butyrate. In another embodiment, said preparation according to the invention, wherein calcium butyrate is comprised in a gastro-resistant formulation, comprises about 93% by weight of calcium butyrate and about 7% of hardened palm oil. Such a formulation comprises about 75% by weight of butyrate. Preferably, these formulations also provide extended release of the butyrate over the length of the intestine.

In a further embodiment, said preparation according to the invention, wherein the gastro-resistant formulation is in the form of a granules, is preferably encapsulated or in the form of a tablet. Enclosing the granules in a capsule may provide ease of dosing and/or ease of oral administration. Having the granules in the form of a tablet also provides ease of dosing and/or oral administration.

In another embodiment, a kit is provided comprising a combination of a gastro-resistant formulation for oral administration as described above, including capsules or tablets comprising such formulations, and a suppository for insertion in the rectum as described above. Such a kit may be advantageous when e.g. oral administration may not result in optimal butyrate delivery along the entire length of the intestine, when e.g. at the distal end of the intestine butyrate levels in the intestine are too long. In such a scenario, delivery of butyrate via a suppository may result in delivery of butyrate at the distal end. Combined, delivery both orally and via the rectum may result in sufficient butyrate levels over the entire length of the intestine.

In one embodiment, a preparation comprising a butyrate salt for enteral administration according to the invention is provided, wherein the preparation is for use in the treatment of osteoarthritis. Surprisingly, the inventors found that when orally administering a butyrate salt, in an extended release formulation in accordance with the invention, to patients suffering from osteoarthritis that symptoms related to this disease such as joint pain severely reduced. Without being bound by theory, osteoarthritis hence can be regarded to be a disease that may be associated with systemic inflammation, e.g. with bacterial products like lipopolysaccharides and peptidoglycans in the circulation that may induce the synthesis and release of pro-inflammatory cytokines. Such bacterial products and bacterial DNA can also be found in the inflamed lesions causing the local inflammation (Toivanen Ann Rheum Dis. 2003 September; 62(9):807-11). The inventors realized that further diseases that may also have an association with systemic inflammation may also benefit from a treatment with butyrate. Thus, in another embodiment, a preparation comprising a butyrate salt for enteral administration according to the invention is provided, wherein the preparation is for use in the treatment of rheumatism. Rheumatism is also a disease that may be associated with systemic inflammation.

Hence, in a another embodiment, a preparation comprising a butyrate salt for enteral administration according to the invention is provided, wherein the preparation is for use in the treatment of gout. As shown in the examples, subjects suffering from gout also benefited from butyrate. Without being bound by theory, gout may also be associated with systemic inflammation. In addition, the intestinal epithelium also has Breast Cancer Receptor Protein receptors (BCRP). As these receptors also can function as uric acid transporters, the administration of butyrate can assist in lowering the uric acid concentration in the blood being beneficial for subjects suffering from gout as well.

In one embodiment, a preparation comprising a butyrate salt for enteral administration according to the invention is provided, wherein the preparation is for use in the treatment of impaired kidney functioning. As shown above, the administration of butyrate salt to the intestine may have lowering effects on concentrations of uric acid in the blood and of bacterial components. Such lowering effects may be highly beneficial in subjects suffering from impaired kidney functioning, In yet another embodiment, a preparation comprising a butyrate salt for enteral administration according to the invention is provided, wherein the preparation is for use in the treatment of autoimmune diseases. Autoimmune diseases in general may also be associated with systemic inflammation. Hence, in a further embodiment, a preparation comprising a butyrate salt for enteral administration according to the invention is provided, wherein the preparation is for use in the treatment of psoriasis or for use in the treatment of multiple sclerosis.

In one embodiment, a preparation comprising a butyrate salt for enteral administration according to the invention is provided, wherein the preparation is for use in the treatment of arteriosclerosis. As vascular plaques often comprise bacteria that can be derived from the intestine, e.g. enterobacterial colonization and arteriosclerosis may also be associated with systemic inflammation, the use of butyrate may therefore also be beneficial for subjects suffering from arteriosclerosis.

It was also observed by subjects taking daily dosages of butyrate salts for enteral administration that cognitive improvements occurred. Subjects reported clearer thinking. Hence, the enteral administration of butyrate salts in accordance with the invention may be beneficial for the treatments of neurological diseases. In one embodiment, a preparation comprising a butyrate salt for enteral administration according to the invention is provided, wherein the preparation is for use in the treatment of Alzheimer's disease. In another embodiment, a preparation comprising a butyrate salt for enteral administration according to the invention is provided, wherein the preparation is for use in the treatment of Parkinson's disease. In yet another embodiment, a preparation comprising a butyrate salt for enteral administration according to the invention is provided, wherein the preparation is for use in the treatment of autism. In one embodiment, a preparation comprising a butyrate salt for enteral administration according to the invention is provided, wherein the preparation is for use in the treatment of depression. Systemic inflammation has also been implicated in these neurological diseases as one of the factors contributing thereto. Hence, without being bound by theory, subjects suffering from such diseases may benefit because systemic inflammation can be reduced and/or the functioning of the nervous system may be improved.

In one embodiment, a preparation comprising a butyrate salt for enteral administration according to the invention is provided, wherein the preparation is for use in the treatment of migraine. The pain sensation in migraine can be caused by an inflammatory process in the meninges. Hence, subjects suffering from migraine that are in a state of systemic inflammation may benefit from the treatment with butyrate in accordance with the invention resulting from e.g. a diminishing of systemic inflammation, and the pain associated with migraine attacks.

A hangover is the temporary, unpleasant physical condition, typically characterized by headache and nausea, following the consumption of an excessive amount of alcohol. In one embodiment, a preparation comprising a butyrate salt for enteral administration according to the invention is provided, wherein the preparation is for use in the treatment of a hangover This effect was reported as a positive side effect by subjects that were taking butyrate according to the invention. This effect may not necessarily be associated with systemic inflammation.

In one embodiment, a preparation comprising a butyrate salt for enteral administration according to the invention is provided, wherein the preparation is for use in the treatment of idiopathic subfertility. As shown in the examples, subjects suffering from idiopathic subfertility highly benefited from the administration of butyrate in accordance with the invention. Hence, without being bound by theory, subjects suffering from diseases or conditions of the reproductive system may be benefit from reducing the inflammatory state. Hence, in a further embodiment, a preparation comprising a butyrate salt for enteral administration according to the invention is provided, wherein the preparation is for use in the treatment of recurrent abortion. In another embodiment, a preparation comprising a butyrate salt for enteral administration according to the invention is provided, wherein the preparation is for use in the treatment of recurrent implantation failure.

EXAMPLES

Example 1

Ten man and women, aged between 25 and 70, all suffering from osteoarthritis and not treated with medicines to treat their rheumatism, were selected. A titration study was performed with two types of Microbead Encapsulated Calcium Butyrate (MECaB), MECaB40 and MECa75. MECaB40 contains about 40% butyrate, about 10% Calcium and about 50% hardened palm oil; for MECaB75 these figures are about 75% butyrate, about 18% calcium and about 7% hardened palm oil. The percentages are by weight.

In animal studies it was found that the kinetics of dissolution of these two forms did not differ. This was confirmed in the study with humans. The coating is essential for intact passage of the stomach, the butyrate comes available along the length of the intestine. In this study it was found that 2× a day an equivalent dose of 350 mg butyrate (total 700 mg) was a suitable minimum dose. For this reason we took 800 mg a day (2× 400 mg) as the effective minimum dose.

Twenty people were included in the next study. It is was descriptive open study. All participants suffered from osteoarthritis from hand and or foot joints. The pain was easily assessable by pinching the joints. No data of rheumatic factor or antibodies to cyclic citrullinated peptide were available. These people had no other reported health complains. No intestinal problems, no pain in the lower abdominal region. Some (12 out of 20) had constipation problems. This group of 20 people used two times a day MECaB75 for the duration of six month, with a daily dose equal to 800 mg butyrate (in the form of 2× 530 mg MECaB75).

Each day the participants made notes of how they experienced the pain. In all 20 participants the pain disappears in a period of 10 to 14 days. The painful swelling disappeared and all participants had full use of the hands and feet; they had not experienced a life without pain for many years. If a participant stopped with the intake of MECaB, painful joints returned within a week. All participants continued the use of the MECaB75 after the duration of the trial. Participants with constipation problems reported normal defecation after the start of the use of the butyrate form.

Example 2

A group of 20 male volunteers with gout complains, associated with severe pain attacks hand, wrist, foot and ankle joints, were selected. Some of them used Allopurinol or colchicine, but only on a temporal base. The BMI varied between 22 and 32 kg/m2. Gout was diagnosed only by clinical features. The initial serum value of uric acid was assessed. This was 7.9±1.9 mg/dl (0.47±0.11 mmol/L; mean±SD). It was apparent that gout was associated with the way of life of these males, which can be described as a Burgundian lifestyle. It was also apparent that the severity of the gout attacks was increased with the increase of the BMI. These men did not change their way of life during the period of observation. The period of observation was 6 month.

The subjects started the daily intake of MECaB75. MECaB75 is formed by microbeads of calcium butyrate coated with hardened palm oil. MECaB75 contains about 75% butyrate, about 18% calcium and about 7% palm oil. The daily intake was 2× 400 (390-410) mg butyrate in the form of MECaB75. One gram of MECaB75 contains about 750 mg butyrate, 180 mg calcium and 70 mg palm oil.

In all participants the gout complaints disappeared and no gout medicine were needed anymore. If a gout attack occurred it was because the participant had forgotten to take his daily dose for a few days. As soon the daily dosing was resumed, the gout attacks disappeared.

It was even noticed by some subjects that had taken some extra MECaB75 (like 0.535 grams, corresponding to an additional dose of 400 (390-410) mg butyrate) before having a heavy meal or drinking wine or beer, that intake of MECaB75 severely reduced or protected from hangovers. The initial serum value of uric acid was assessed. This was 7.9±1.9 mg/dl (0.47±0.11 mmol/L; mean±SD). After one week of use the serum value of uric acid decreased to 6.4±1.7 mg/dl (0.38±0.09 mmol/L; p<0.001; mean value±SD)

Participants with constipation reported that constipations problems disappeared after a few days to a week after starting the daily intake of MECaB75 and defecation without problems was restored.

Example 3

A group of 28 patients with idiopathic subfertility participated in a study.

The plasma concentration of the cytokines sTNFR1 and IL-6 were determined. (sTNFR1:Quantikine ELISA Kit (cat. nr. DRT100); IL-6 Quantikine ELISA Kit (cat. nr. D6050), both from R&D Systems Inc., Minneapolis, USA).

The 28 patients with fertility problems participated in an open randomized control study. One arm was subjected to a daily treatment with butyrate in an gastro-resistant formulation, the other arm was the placebo arm. The daily intake was 2× 400 (390-410) mg butyrate in the form of calcium butyrate in a gastro-resistant formulation with hardened palm oil (one capsule contains 535 mg of the material, or 535 mg of the placebo (just hardened palm oil)). The duration of the study was eight weeks; 14 got placebo and 14 got the butyrate. At the start of the study and 8 weeks later blood plasma IL-6 and sTNFR1 were assessed. The median values were IL-62.6 pg/ml and sTNFR1 1890 pg/ml. After 8 weeks the median values of the experimental group were: Il-61.7 pg/ml and sTNFR1 1190 pg/ml. These were significantly different from the of the untreated group (p<0.05); the median values in the untreated group did not change significantly.

Six women left the study. The remaining 22 women were offered to start or to continue the use of butyrate for a maximum period of 12 month. They were advised to stop the use of butyrate as soon as they got pregnant. They were asked to inform us as soon as a pregnancy was noticed. Of these 22 women 14 conceived within 12 months. This gives an average conception rate or ±9% per month. In our patient population with idiopathic subfertility which are not actively treated and have unprotected intercourse, the conception rate is 5.0% per month (life birth rate 3.8%). In our group of patients with idiopathic subfertility treated daily with gastro-resistant butyrate the monthly conception rate increased to 9%.

Example 4

Multiple sclerosis (MS) is a chronic inflammatory demyelinating disease of the central nervous system with a pathogenesis involving a dysfunctional blood-brain barrier and myelin-specific, autoreactive T cells. The balance between Th1/Th17 en Treg cells is disturbed and patients are in a pro-inflammatory state of the innate immune system. Hence, as MS disease also can be associated with systemic inflammation, we sought out whether subjects suffering from this disease could also benefit from butyrate treatment.

We tested a group of patients with Relapsing-Remitting Multiple Sclerosis (RRMS). Participants consisted of subjects who met the 2010 McDonald Committee criteria for RRMS (Polman C H et al. Ann Neurol. 2011 February; 69(2):292-302.). All had Expended Disability Status Scales scores <2. All subjects were newly diagnosed. These patients declined standard disease-modifying treatment (DMT). We urged these patients to accept DMT since it is well known in the art that the sooner DMT is initiated the better the long term outcome will be. However, they declined DMT because they needed more time to accept the disease and the proposed DMT. They could contact the clinic any time to start DMT. In the transition time we offered treatment with MECa75 for a maximum period of six month. The daily intake was 2× 400 (390-410) mg butyrate in the form of calcium butyrate in a gastro-resistant formulation with hardened palm oil (one capsule MECaB75 contains 535 mg of the gastro-resistant formulation). Twenty patients were included. In total there were 120 observational months. No relapses were reported. According to our historical records we could expect 7.2 relapses in a comparable group of patients without DMT (p<0.05). It is concluded that gastro-resistant butyrate can contribute to the treatment of RRMS.

Example 5

Migraine is a neurological disease characterized by recurrent moderate to severe headaches not only affecting one half of the head sequentially, but the whole body is severely ill. During a migraine attack people feel miserable. The pathogenesis of migraine is complex and multifaceted. The condition is associated with sterile inflammation and hypersensitization of pain pathways. Calcitonin gene related peptide (CGRP) and mast cell degranulation plays a central role in neurogenic inflammation. There is also and increased release of several pro-inflammatory cytokines, especially IL-1, 11-6, 11-8 and TNFα. CGRP and these interleukins are also of pivotal importance by osteoarthritis. Demonstrating similarities between these two diseases. A migraine attack can be accompanied by intestinal inconveniences like constipation or diarrhoea indicating that a disturbed intestinal functioning may be part of a migraine attack. Hence, as migraine may be associated with systemic inflammation and intestinal functioning, we investigated whether subjects suffering from migraine attacks could also benefit from butyrate treatment.

In an open inventory study we asked 20 migraine sufferers to keep notes of medicine use (triptans and NSAIDs), the severity of the pain during migraine attacks and of their intestinal problems (constipation, diarrhoea). After one month without intervention and describing the migraine attack and medicine consumption, they were treated for the duration of 2 months with MECaB75. Four persons did not have any benefit of the treatment. Sixteen reported benefits of the treatment. The average number of migraine days was in the first month 6.5, this number decreased to 5.0 days (average of two the treatment months). The average number of units of NSAIDS (tablets, capsules) decrease with 3.1 (average of two treatment months). The mean number of days with constipation was reduced (from 1.5 to 0.6 (average of two treatment month). All these differences were significantly different (p<0.05). It is concluded that treatment with MECaB75 can contribute to the wellbeing of migraine sufferers.

Example 6

Parkinson's Disease (PD) is hypothesized to have its origin in the intestine. The inflammatory agent in Parkinson's disease is misfolded (β folding) α-synuclein, a protein abundant present in nerve cells. In Lewy bodies and neurites aggregates of phosphorylated misfolded α-synuclein are the major constituent in PD patients. α-Synuclein can be found in nerve cells of the gastrointestinal tract from oesophagus to rectum. The first traces of PD can be found in Lewy bodies and neurites in intestinal nerves. The β folded α-synuclein proteins is believed to migrate to the CNS system and in the substantia nigra. Here they activate glia cells and provoke inflammatory processes, the equilibrium between T1/T17 and Treg is disturbed in a pro-inflammatory direction and pro-inflammatory cytokines are produced. The inflammatory process destroys the dopamine producing nerve cells resulting in shortage of dopamine and the characteristic movements associated with PD.

The misfolding of α-synuclein is comparable with that of prions. Prion diseases are to this date not curable and hence, as is PD. However, there are promising results with treatments with antibodies that target α-synuclein. PD is also associated with many conditions and symptoms amongst which impaired barrier function of the intestine and with local increased synthesis of pro-inflammatory cytokines. PD patients have often small intestine bacterial overgrowth and infections of the small intestine of Helicobacter. It has been shown that treatment with antibiotics and irradiation of the Helicobacter infection the condition of PD patients may be improved and slow down the progression of the disease.

We hypothesized that restoring normal intestinal permeability, that may reduce the synthesis of pro-inflammatory cytokines by cells of the intestine, lamina propria and splanchnic area, thereby reducing i.a. systemic inflammation, the progress of PD can be slowed down and the quality of life of PD patients will improve.

We selected 10 patients with long lasting PD (5 years after initial diagnosis), all with constipation problems. Constipation is also often associated with PD. Patients were treated for at least 3 months with 2× 400 calcium butyrate in the form MECaB75 (capsules containing 535 mg of the material). All 10 had a relieve of the constipation problems after two weeks and reported increased quality of life. They reported feeling less stiff.

The invention claimed is:

1. A method of treatment of a disease associated with systemic inflammation in a subject, comprising
delivering an oral administration of a preparation comprising a therapeutically-effective amount of a butyrate salt to the subject having a disease associated with systemic inflammation, wherein the preparation comprises butyrate salt in a gastro-resistant formulation, and wherein the disease associated with systemic inflammation is selected from the group consisting of osteoarthritis, Parkinson's disease, migraine, idiopathic subfertility, hangover, and gout.

2. The method of claim 1, wherein the gastro-resistant formulation is configured to release butyrate in the intestinal tract.

3. The method of claim 1, wherein the use comprises a daily intake of at most 4 grams of butyrate.

4. The method of claim 1, wherein the butyrate salt is calcium butyrate.

5. The method of claim 1, wherein the gastro-resistant formulation comprises a triglyceride matrix.

6. The method of claim 5, wherein said triglyceride matrix comprises hardened palm oil.

7. The method of claim 1, wherein the gastro-resistant formulation comprises about 50% (w/w) calcium butyrate, and about 50% (w/w) hardened palm oil, or about 93% (w/w) calcium butyrate, and about 7% (w/w) hardened palm oil.

8. The method of claim 1, wherein the gastro-resistant formulation is in the form of a granulate, wherein the granulate comprises butyrate salt granules of 0.5-1.5 mm.

9. The method of claim 2, wherein the use comprises a daily intake of at most 4 grams of butyrate.

10. The method of claim 2, wherein the butyrate salt is calcium butyrate.

11. The method of claim 3, wherein the butyrate salt is calcium butyrate.

12. The method of claim 2, wherein the gastro-resistant formulation comprises a triglyceride matrix.

13. The method of claim 3, wherein the gastro-resistant formulation comprises a triglyceride matrix.

14. The method of claim 12, wherein said triglyceride matrix comprises hardened palm oil.

15. The method of claim 13, wherein said triglyceride matrix comprises hardened palm oil.

16. The method of claim 2, wherein the gastro-resistant formulation comprises about 50% (w/w) calcium butyrate, and about 50% (w/w) hardened palm oil, or about 93% (w/w) calcium butyrate, and about 7% (w/w) hardened palm oil.

17. The method of claim 2, wherein the gastro-resistant formulation is in the form of a granulate, wherein the granulate comprises butyrate salt granules of 0.5-1.5 mm.

18. The method of claim 1, wherein the gastro-resistant formulation is configured to release butyrate in the intestinal tract in an extended way along the entire length of the intestinal tract.

19. The method of claim 1, wherein the therapeutically-effective amount is an amount of butyrate comprising a twice-daily administration to the subject totaling at least 800 mg.

* * * * *